US00PP36498P2

(12) United States Plant Patent
Giesen

(10) Patent No.: US PP36,498 P2
(45) Date of Patent: Feb. 25, 2025

(54) ***PETUNIA* PLANT NAMED 'PEHY0084'**

(50) Latin Name: *Petunia hybrida*
Varietal Denomination: PEHY0084

(71) Applicant: SYNGENTA CROP PROTECTION AG, Basel (CH)

(72) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,971

(22) Filed: Apr. 23, 2024

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./263.1, 356.1, 356.13
See application file for complete search history.

(56) References Cited

U.S. PATENT DOCUMENTS

PP31,672 P2 * 4/2020 Kerley ..... A01H 5/02
Plt./356.13

* cited by examiner

*Primary Examiner* — Karen M Redden
(74) *Attorney, Agent, or Firm* — Dale Skalla

(57) ABSTRACT

A new *Petunia* plant named 'PEHY0084' particularly distinguished by its mounding, upright plant habit, medium sized flowers, a unique purple flower color with a white flower edge and a white flower center and its early flowering.

1 Drawing Sheet

Latin name of the genus and species of the plant claimed: *Petunia hybrida.*
Varietal denomination: 'PEHY0084'.

BACKGROUND OF THE NEW PLANT

The present invention comprises a new *Petunia*, botanically known as *Petunia hybrida*, and hereinafter referred to by the variety name 'PEHY0084'.

'PEHY0084' is a product of a planned breeding program. The new cultivar has a mounding, upright plant habit, medium sized flowers, a unique purple flower color with a white flower edge and a white flower center and is early flowering.

'PEHY0084' originated from a hybridization made in October 2019 in a controlled breeding environment in Enkhuizen, The Netherlands. The female parent was the unpatented, proprietary selection 'PETBE0475-3V'. Compared to 'PEHY0084', it has more upright plant shape, dark purple flower color with a broad white edge and larger flowers.

The male parent of 'PEHY0084' was the unpatented, proprietary selection 'PETBE0497-2V'. Compared to 'PEHY0084', it is more trailing plant habit, earlier in flowering, and it has a dark purple flower color with a larger white edge.

The resulting seeds were sown in February 2020. 'PEHY0084' was selected as one flowering plant within the progeny of the stated cross in October 2019 in a controlled environment in Enkhuizen, The Netherlands.

The first act of asexual reproduction of 'PEHY0084' was accomplished when vegetative cuttings were propagated from the initial selection in April 2020 in a controlled environment in Enkhuizen, The Netherlands.

BRIEF SUMMARY OF INVENTION

Horticultural examination of plants grown from cuttings of the plant initiated in April 2020 and continuing thereafter, has demonstrated that the combination of characteristics as herein disclosed for 'PEHY0084' are firmly fixed and are retained through successive generations of asexual reproduction.

'PEHY0084' has not been observed under all possible environmental conditions. The phenotype may vary significantly with variations in environment such as temperature, light intensity, and day length.

A Plant Breeder's Right for this cultivar has not yet been applied for. 'PEHY0084' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0084' with colors being as true as possible with an illustration of this type.

Figure 1:
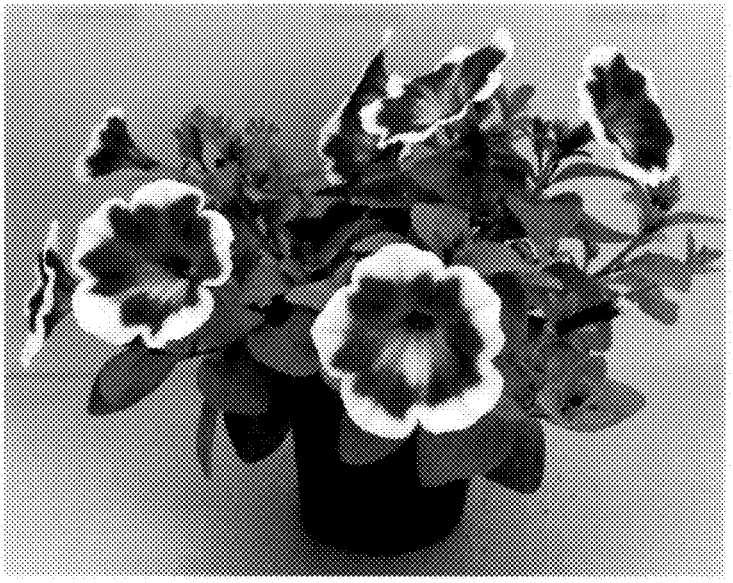
Figure 2:
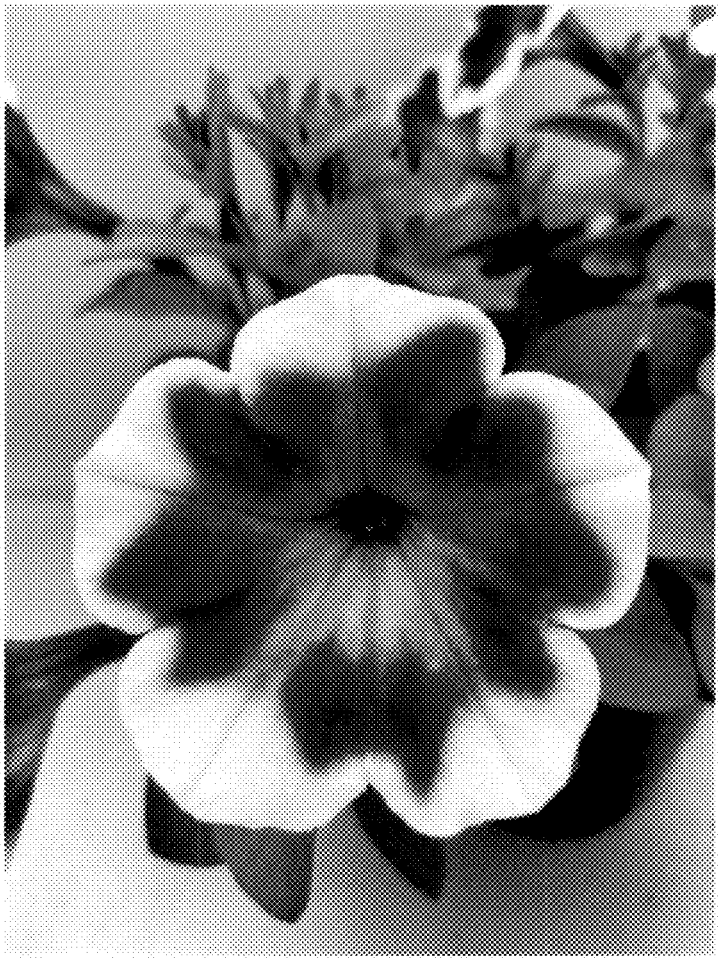

The photographic drawings show in FIG. 1 a flowering plant of the new variety and in FIG. 2 a close-up of the flowers.

DETAILED BOTANICAL DESCRIPTION

The afore mentioned photographs were taken in April 2024 from plants growing indoor in 11 cm pots in Andijk, The Netherlands. These plants were approximately 10 weeks of age.

The plant descriptions and measurements were taken on the same plants as the pictures in April 24 in Andijk, The Netherlands on outdoor plants grown in full soil. These plants were about 10 weeks old.

Color references are made to The Royal Horticultural Society Colour Chart (R.H.S.) 2001.

TABLE 1

DIFFERENCES BETWEEN THE NEW VARIETY 'PEHY0084' AND A SIMILAR VARIETY

| | 'PEHY0084' | 'Sunsurfpafure', U.S. Plant Pat. No. 18,616 |
|---|---|---|
| Flower color: | Purple with broad white edge and white centre | Dark Purple with small white edge |
| Stem length: | Short to medium stem length | Long stem length |
| Flower Size: | Medium size flower | Large size flower |

Plant:
- *Form, growth and habit.*—Mounding plant habit.
- *Plant height.*—22 cm.
- *Plant height (inflorescence included).*—26 cm.
- *Plant diameter (width).*—Approximately 40 cm.

Roots:
- *Number of days to initiate and produce roots.*—16 days at about 22° C.
- *Type.*—Fine, fibrous, free branching.
- *Color.*—RHS N157C.

Foliage:
- *Arrangement.*—Alternate, simple; sometimes opposite, decussate.
- *Immature leaf, color upper surface.*—RHS 137B.
- *Immature leaf, color lower surface.*—RHS 137C.
- *Mature leaf, color upper surface.*—RHS 138B.
- *Mature leaf, color lower surface.*—RHS 138C.
- *Length.*—3.8-4.8 cm.
- *Width.*—2.8 cm.
- *Shape.*—Ovate.
- *Base shape.*—Acuminate.
- *Apex shape.*—Acute.
- *Margin.*—Entire.
- *Texture, upper surface.*—Densely covered with short hairs.
- *Lower surface.*—Densely covered with short hairs.
- *Color of veins, upper surface.*—RHS 138A.
- *Color of veins, lower surface.*—RHS 138A.
- *Petiole color.*—RHS 138A.
- *Length.*—0.2 cm.
- *Diameter.*—0.2 cm.
- *Petiole texture.*—Densely covered with short hairs.

Stem:
- *Quantity of main branches per plant.*—5-6.
- *Color of stem.*—RHS 138B.
- *Length of stem.*—24 cm.
- *Diameter.*—0.3-0.4 cm.
- *Length of internodes.*—1.4-2.4 cm.
- *Texture.*—Dense, mostly glandular short hairs.
- *Color of pedicel.*—RHS 137D.
- *Length of pedicel.*—1.6 cm.
- *Diameter of pedicel.*—0.3 cm.
- *Texture of pedicel.*—Densely covered with short hairs.

Inflorescence:
- *Type.*—Flowers solitary in upper leaf axis.
- *Floret type.*—Funnel-shaped; 5 lobed petals. fused at base.
- *Blooming habit.*—Rather early flowering in greenhouse, flowering throughout the summer months.
- *Quantity of inflorescences per plant.*—Approximately 40.
- *Lastingness of individual blooms on the plant.*—About 7 days.
- *Fragrance.*—Some little smell.

Bud (just when opening):
- *Color.*—RHS N80A at top, RHS N80B towards base.
- *Length.*—4.0 cm.
- *Width.*—0.7 cm.
- *Shape.*—Oblong.

Immature inflorescence:
- *Flower horizontal diameter.*—4.9 cm.
- *Color petals, upper surface.*—RHS 78A.
- *Color petals, lower surface.*—RHS 77C.

Mature flower:
- *Flower horizontal diameter.*—5.8 cm.
- *Flower height (vertical).*—3.8 cm.
- *Color upper surface.*—Primary color; RHS 78A secondary color; RHS 155A (white edge).
- *Color lower surface.*—RHS 78B.
- *Conspicuousness of veins.*—Very little.
- *Apex shape.*—Acuminate.
- *Margin.*—Entire.
- *Waviness of margin.*—Medium.
- *Petal lobation.*—Medium.
- *Petal texture, upper surface.*—Smooth.
- *Petal texture, lower surface.*—Smooth, occasionally a short hair mainly along veins.
- *Corolla tube color outside.*—RHS 78D.
- *Corolla tube color inside.*—RHS 76C deep in throat; RHS 78A toward petals.
- *Conspicuousness of veins in tube.*—Very little.
- *Corolla tube length.*—2.6 cm.
- *Corolla tube texture, outside.*—Dense and short glandular hairs.
- *Corolla tube texture, inside.*—Glabrous.

Calyx:
- *Color of sepal, upper surface.*—RHS 136A.
- *Color of sepal, lower surface.*—RHS 136B.
- *Length.*—1.3 cm.
- *Width.*—0.2-0.3 cm.
- *Shape.*—Ensiform.
- *Apex shape.*—Acute.
- *Base.*—Fused.
- *Margins.*—Entire.
- *Texture, upper surface.*—Covered with short glandular hairs.
- *Lower surface.*—Covered with short glandular hairs.

Reproductive organs:
- *Pistil.*—1.
- *Length.*—2.1 cm.
- *Style color.*—RHS 145A.
- *Style length.*—1.7 cm.
- *Stigma color.*—RHS 145B.
- *Stamens.*—
- *Quantity per flower.*—5.
- *Color of filaments.*—RHS 151B.
- *Length filaments.*—1.9 cm.
- *Anther color.*—RHS 81C.
- *Anther length.*—0.2 cm.
- *Anther shape.*—Elliptical.
- *Color of pollen.*—RHS 158B.
- *Pollen amount.*—Abundant.
- *Fertility/seed set.*—Has not been observed on this hybrid.
- *Disease/pest resistance.*—Has not been observed on this hybrid.

What is claimed is:

1. A new and distinct variety of *Petunia* plant named 'PEHY0084' substantially as illustrated and described herein.

* * * * *